(12) United States Patent
Cavazza

(10) Patent No.: US 8,198,260 B2
(45) Date of Patent: *Jun. 12, 2012

(54) COMPOSITION FOR THE PREVENTION AND/OR TREATMENT OF DISORDERS DUE TO ABNORMAL LIPID METABOLISM, COMPRISING PROPIONYL L-CARNITINE AND CHITOSAN

(75) Inventor: Claudio Cavazza, Rome (IT)

(73) Assignee: Sigma-Tau Industrie Farmaceutiche Riunite SpA, Rome (IT)

( * ) Notice: Subject to any disclaimer, the term of this patent is extended or adjusted under 35 U.S.C. 154(b) by 152 days.

This patent is subject to a terminal disclaimer.

(21) Appl. No.: 10/863,325

(22) Filed: Jun. 9, 2004

(65) Prior Publication Data

US 2005/0020538 A1  Jan. 27, 2005

Related U.S. Application Data

(62) Division of application No. 10/130,481, filed as application No. PCT/IT00/00462 on Nov. 14, 2000, now Pat. No. 6,780,851.

(30) Foreign Application Priority Data

Nov. 18, 1999 (IT) .................. RM99A0707

(51) Int. Cl.
- *A01N 43/04* (2006.01)
- *A01N 47/00* (2006.01)
- *C08B 37/08* (2006.01)
- *C07H 1/00* (2006.01)

(52) U.S. Cl. ............ 514/55; 514/909; 536/20; 536/124
(58) Field of Classification Search .................. 536/20, 536/124; 514/55, 909
See application file for complete search history.

(56) References Cited

U.S. PATENT DOCUMENTS

| 4,255,449 A * | 3/1981 | Cavazza ................. 514/554 |
| 4,343,816 A | 8/1982 | Cavazza |
| 6,323,189 B1 * | 11/2001 | Hardinge-Lyme ............ 514/55 |

FOREIGN PATENT DOCUMENTS

| EP | 0 951 909 A | 10/1999 |
| JP | 11263733 A | 9/1999 |
| JP | 11263733 A | 9/1999 |

OTHER PUBLICATIONS

Spagnoli et al ("Propionyl-L-carnitine prevents the progression of atherosclerotic lesions in aged hyperliemic rabbits", Atherosclerosis 114 (1995), p. 29-44).*

Dyslipidemia from Merck Manual Sep. 2008.

* cited by examiner

*Primary Examiner* — Shaojia Anna Jiang
*Assistant Examiner* — Everett White
(74) *Attorney, Agent, or Firm* — Lucas & Mercanti, LLP

(57) ABSTRACT

A composition is disclosed suitable for the prevention and/or treatment of disorders due to abnormal lipid metabolism, such as hypercholesterolaemia, atherosclerosis, hyperlipidaemia and obesity, and which can therefore take the form of a dietary supplement or of an actual medicine, comprising as characterizing active ingredients: (a) propionyl L-carnitine or a pharmacologically acceptable salt thereof, and (b) chitosan or its derivatives and congeners.

2 Claims, No Drawings

COMPOSITION FOR THE PREVENTION AND/OR TREATMENT OF DISORDERS DUE TO ABNORMAL LIPID METABOLISM, COMPRISING PROPIONYL L-CARNITINE AND CHITOSAN

CROSS REFERENCE TO RELATED APPLICATION

This application is a divisional of application Ser. No. 10/130,481, filed May 20, 2002, now U.S. Pat. No. 6,780,851, which in turn is a U.S. national phase of PCT/IT00/00462 filed Nov. 14, 2000.

The present invention relates to a composition suitable for the prevention and/or treatment of disorders due to abnormal lipid metabolism, such as hypercholesterolaemia, atherosclerosis, hyperlipidaemia and obesity, comprising as characterising active ingredients propionyl L-carnitine or a pharmacologically acceptable salt thereof, and chitosan or its derivatives and congeners.

Correspondingly, the composition may take the form and exert the activity of a dietary supplement or of an actual medicine, depending upon the support or preventive action or the strictly therapeutic action which the composition is intended to exert according to the particular individuals for whom it is to be used.

The action of the carnitines in general, and of propionyl L-carnitine in particular, on lipid metabolism is well known, as is their anti-atherosclerotic action and their action on lipid metabolism disorders.

The carnitines activate the processes of β-oxidation of intra-mitochondrial fatty acids and the oxidation of branched-chain amino acids, as well as regulating insulin activity. In particular, propionyl L-carnitine is capable of stabilising the phospholipid membranes and the deformability of erythrocytes, as well as of acting on lipid peroxidation phenomena.

All these properties of the carnitines, and particularly of propionyl L-carnitine, therefore emphasise their importance in the regulation of the metabolism of lipids and related phenomena such as atherosclerosis, hypercholesterolaemia, hypertriglyceridaemia, lipid accumulation and weight gain.

In the same sense, though with a different mechanism, a class of substances known as chitosans may take effect on lipid metabolism. The chitosans consist mainly of naturally occurring chitins of a polysaccharide type present above all in the exodermal part of shellfish in the form of poly-β-1,4-acetylglucosamine, the de-acetylation of which can lead to simpler structures such as poly-β-1,4-D-glucosamine, which also determine a greater solubility of the product related to the lower molecular weight which may range from 100,000 to 1,000 according to the procedure used for preparing the various oligomers.

The main characteristic of these products is related to their lipophilicity and consists, via their basic charges, in binding to fatty acids, preventing their absorption, for instance, at the intestinal level.

Experiments conducted in animals treated with chitosan have, in fact, demonstrated its efficacy in reducing hypercholesterolaemia, as well as serum and hepatic lipids, while experiments in human subjects have demonstrated its efficacy particularly in diets suitable for reducing body weight and in obese patients.

The lipid-lowering and weight-reducing effect of chitosan occurs fairly rapidly, and no signs of intolerance or toxicity have been reported in the course of its use.

It has now surprisingly been found that a composition containing as its characterising active ingredients:

(a) propionyl L-carnitine or a pharmacologically acceptable salt thereof, and
(b) chitosan or its derivatives or congeners is particularly useful, thanks to an unexpected, potent synergistic action between the components, in the prevention and/or treatment of disorders due to abnormal lipid metabolism, such as hypercholesterolaemia, atherosclerosis, hyperlipidaemia and obesity.

It has also been found that, advantageously, component (a) may additionally contain a "carnitine" selected from the group consisting of acetyl L-carnitine, valeryl L-carnitine, isovaleryl L-carnitine and butyryl L-carnitine or a pharmacologically acceptable salt thereof or mixtures thereof.

In the composition of the present invention, the weight ratio of (a) to (b) may range from 1:1 to 1:5, and preferably from 1:1 to 1:3.

The composition of the present invention may further comprise vitamins, coenzymes, mineral substances, amino acids and anti-oxidants.

The new composition, which is the object of the present invention, exploits the favourable activities exerted on lipid metabolism and on absorption of fats by alkanoyl L-carnitines, and particularly propionyl L-carnitine, or by propionyl L-carnitine together with acetyl L-carnitine, valeryl L-carnitine, isovaleryl L-carnitine and/or butyryl L-carnitine, or a pharmacologically acceptable salt thereof, when these are combined with chitosan or its congeners, achieving an unexpected and surprising synergistic effect between its components which is extremely advantageous for exploitation in the field of the prevention and treatment of disorders due to abnormal lipid metabolism, such as hypercholesterolaemia, atherosclerosis, hyperlipidaemia and obesity.

Experimental Atherosclerosis Tests

According to the regimen suggested by Malinow (Malinow M. R., *Atherosclerosis*, 4:105, 1983) an atherogenic diet consisting of 24% casein, 10% cotton oil, 5% sodium chloride, 60% sugar, 1% cholesterol, and Vit. $D_2$ 200 mUST/g diet was administered for six weeks consecutively to different groups of male Wistar rats.

While one group of rats served as a control group, the other groups were administered chitosan (100 mg/kg) or propionyl L-carnitine (100 mg/kg) or chitosan (100 mg/kg) plus propionyl L-carnitine (100 mg/kg).

Another group of animals was administered acetyl L-carnitine (100 mg/kg) and butyryl L-carnitine (100 mg/kg) in addition to chitosan and propionyl L-carnitine.

The results of these tests demonstrated a substantial protective effect against the atherosclerotic lesions induced by the atherogenic diet by both propionyl L-carnitine and by chitosan, but surprisingly the maximum protective effect was detectable when chitosan was combined with propionyl L-carnitine.

In this group of rats, in fact, morphometric measurement of the thickness of the abdominal aorta and the intensity of the staining induced by Sudan IV reveal a substantial synergistic action of the protective effect afforded by the combination of the two components. The protection appears even more marked with the combination of the various alkanoyl L-carnitines (propionyl L-carnitine, acetyl L-carnitine, butyryl L-carnitine) plus chitosan.

Tests in Experimentally Obese Rats

In these tests, male Wistar rats aged approximately two months were administered a lipogenic diet containing 50% glucose, 20% casein, 4% cellulose, 1% hazel nut oil, 18% starch, 2% vitamin mixture, and 5% salt mixture. The diet was administered for fifteen days consecutively to different groups of rats, one of which served as a control group, whereas the remaining groups were administered daily, per 100 g of diet, 2 g of propionyl L-carnitine or 1 g of chitosan, or the two compounds in combination at the same doses.

Another group was also administered acetyl L-carnitine (2 g/100 g diet) and butyryl L-carnitine (0.5 g/100 g diet) in addition to propionyl L-carnitine and chitosan.

At the end of the fifteenth day since the beginning of the diet, feed consumption and increase in body weight were calculated for each group of rats. The results are presented in Tables 1 and 2 here below.

TABLE 1

Mean daily feed consumption (g)/animal

| | Before treatment | At the end of treatment |
|---|---|---|
| Propionyl L-carnitine | 19.8 ± 0.71 | 18.9 ± 0.50 |
| Chitosan | 18.5 ± 0.45 | 16.6 ± 0.95 |
| Propionyl L-carnitine + chitosan | 19.3 ± 0.60 | 13.1 ± 0.71 |
| Propionyl L-carntine + acetyl L-carnitine + butyryl L-carnitine + chitosan | 18.9 ± 0.55 | 12.5 ± 0.75 |

TABLE 2

Mean body growth

| | Final weight increase |
|---|---|
| Controls | 65.6 ± 4.1 |
| Propionyl L-carnitine | 60.8 ± 5.2 |
| Chitosan | 49.5 ± 3.9 |
| Propionyl L-carnitine + chitosan | 29.7 ± 2.9 |
| Propionyl L-carnitine + acetyl L-carnitine + butyryl L-carnitine + chitosan | 26.3 ± 3.4 |

On the basis of the data presented, there is a marked reduction in body weight together with a reduction in feed consumption, particularly in the group of animals treated with propionyl L-carnitine plus chitosan, thus demonstrating in this case a true synergistic effect between these two compounds.

Tests in Experimentally Hypercholesterolaemic Rabbits

Another type of experiment was conducted in New Zealand rabbits kept on a hypercholesterolaemic diet for forty days and treated with alkanoyl L-carnitine, chitosan or with the two types of compounds in combination. In these tests, 0.5% by weight of cholesterol was added to the normal diet of the rabbits consisting of 150 g/day and containing 2% fats, 20% fibres and 11% ashes.

While one group of animals was used as a control group, the remaining groups were treated for six days with propionyl L-carnitine (2 g/100 g diet), chitosan (1 g/100 g diet), or propionyl L-carnitine+acetyl L-carnitine+butyryl L-carnitine (1 g+1 g+1 g/100 g diet) or with chitosan plus propionyl L-carnitine or chitosan plus the alkanoyl carnitine complex at the doses indicated above.

At the end of the fortieth day of treatment blood samples were taken from the ear vein from all animals and the plasma was used to calculate lipoprotein content in the various fractions (VLDL, LDL, HDL) after ultracentrifuging according to the method described by Noble (Noble R. P., *J. Lipid Res.*, 9:693, 1968). The results of these tests, presented in Table 3 here below, indicate that the increase in VLDL observed in the control animals is much less significant in the animals treated with propionyl L-carnitine, with alkanoyl L-carnitine or with chitosan, but that it is completely inhibited in animals treated with the combination of propionyl L-carnitine plus chitosan or with the alkanoyl carnitin combination plus chitosan.

These experiments, too, indicate the presence of a marked synergistic effect between the alkanoyl L-carnitines and chitosan.

TABLE 3

Plasma lipoprotein concentrations (mg/dl) after 40 days

| | VLDL | LDL | HDL |
|---|---|---|---|
| | Day 0 | | |
| Controls | 1.6 ± 1.1 | 10.6 ± 2.4 | 24.5 ± 3.7 |
| Propionyl L-carnitine | 1.4 ± 0.9 | 9.8 ± 1.9 | 24.2 ± 2.4 |
| Propionyl L-carnitine + acetyl L-carnitine + butyryl L-carnitine | 0.9 ± 1.8 | 12.4 ± 2.4 | 26.8 ± 3.1 |
| Chitosan | 1.7 ± 1.4 | 26.9 ± 8.4 | |
| Chitosan + propionyl L-carnitine | 1.1 ± 1.1 | 13.5 ± 3.5 | 25.4 ± 4.1 |
| Chitosan + propionyl L-carnitine + acetyl L-carnitine + butyryl L-carnitine | 1.3 ± 0.9 | 10.5 ± 3.8 | 27.2 ± 3.5 |
| | Day 40 | | |
| Controls | 1.132 ± 305 | 445 ± 27.4 | 27.4 ± 11.5 |
| Propionyl L-carnitine | 832 ± 105 | 322 ± 31.4 | 26.5 ± 10.4 |
| Propionyl L-carnitine + acetyl L-carnitine + butyryl L-carnitine | 720 ± 205 | 309 ± 27 | 24.4 ± 11.2 |
| Chitosan | 540 ± 55 | 209 ± 20 | 22 ± 12.2 |
| Chitosan + propionyl L-carnitine | 205 ± 19 | 180 ± 15 | 26 ± 9.4 |
| Chitosan + propionyl L-carnitine + acetyl L-carnitine + butyryl L-carnitine | 194 ± 12.4 | 195 ± 11 | 28.2 ± 9.1 |

Illustrative, non-limiting examples of compositions according to the invention are reported hereinbelow.

| | | |
|---|---|---|
| 1) Propionyl L-carnitine | 300 | mg |
| Chitosan (poli-β-1,4-N-acetyl-glucosamine) | 300 | mg |
| 2) Propionyl L-carnitine | 100 | mg |
| Acetyl L-carnitine | 100 | mg |
| Butyryl L-carnitine | 100 | mg |
| Chitosan (poli-β-1,4-N-acetyl-glucosamine) | 300 | mg |
| 3) Propionyl L-carnitine | 600 | mg |
| Chitosan (poli-β-1,4-N-acetyl-glucosamine) | 600 | mg |
| 4) Propionyl L-carnitine | 200 | mg |
| Acetyl L-carnitine | 200 | mg |
| Butyryl L-carnitine | 200 | mg |
| Chitosan (poli-β-1,4-N-acetyl-glucosamine) | 600 | mg |
| 5) Propionyl L-carnitine | 500 | mg |
| Chitosan (poli-β-1,4-N-acetyl-glucosamine) | 500 | mg |
| 6) Propionyl L-carnitine | 200 | mg |
| Acetyl L-carnitine | 200 | mg |
| Butyryl L-carnitine | 200 | mg |
| Chitosan (poli-β-1,4-N-acetyl-glucosamine) | 600 | mg |
| 7) Propionyl L-carnitine | 300 | mg |
| Chitosan (poli-β-1,4-N-acetyl-glucosamine) | 500 | mg |
| Vit. C | 30 | mg |
| Zinc | 1 | mg |
| Chromium | 10 | μg |
| Vanadium | 0.5 | mg |
| Selenium methionine | 30 | μg |
| 8) Propionyl L-carnitine | 500 | mg |
| Chitosan (poli-β-1,4-N-acetyl-glucosamine) | 500 | mg |
| Green tea catechin | 50 | mg |
| Polyphenols of grapes | 100 | mg |
| Resveratrol | 1 | mg |
| Coenzime $Q_{10}$ | 20 | μg |
| 9) Propionyl L-carnitine | 300 | mg |
| Chitosan (poli-β-1,4-N-acetyl-glucosamine) | 500 | mg |
| Vit. C | 100 | mg |
| Piridoxine | 5 | mg |
| β-carotene | 2 | mg |
| Taurine | 100 | mg |
| Vit. PP | 50 | mg |

What is meant by pharmacologically acceptable salt of L-carnitine or alkanoyl L-carnitine is any salt of these active ingredients with an acid that does not give rise to unwanted toxic or side effects. Such salts are well known to pharmacy experts.

Examples of suitable salts, though not exclusively these, are: chloride; bromide; iodide; aspartate, acid aspartate; citrate, acid citrate; tartrate; phosphate, acid phosphate; fumarate; acid fumarate; glycerophosphate; glucose phosphate; lactate; maleate, acid maleate; orotate; oxalate, acid oxalate; sulphate, acid sulphate, trichloroacetate, trifluoroacetate and methanesulphonate.

A list of FDA-approved pharmacologically acceptable salts is given in Int. J. of Pharm. 33, (1986), 201-217; this publication is incorporated herein by reference.

The invention claimed is:

1. A combination composition consisting of:
 (a) propionyl L-carnitine or a pharmacologically acceptable salt thereof, and
 (b) chitosan;
 wherein the weight ratio (a):(b) is from 1:1 to 1:5, said composition being capable of leading to lowering VLDL serum level while leaving the HDL serum level unaffected wherein said combination composition is administered to a mammal in need thereof.

2. The composition of claim 1, wherein the pharmacologically acceptable salt of the propionyl L-carnitine is selected from the group consisting of chloride, bromide, iodide, aspartate, acid aspartate, citrate, acid citrate, tartrate, phosphate, acid phosphate, fumarate, acid fumarate, glycerophosphate, glucose phosphate, lactate, maleate, acid maleate, orotate, oxalate, acid oxalate, sulphate, acid sulphate, trichloroacetate, trifluoroacetate and methane sulfonate.

\* \* \* \* \*